(12) United States Patent
Jiang et al.

(10) Patent No.: US 9,500,844 B2
(45) Date of Patent: Nov. 22, 2016

(54) COMPACT LENS SYSTEM FOR USE IN PHOTOACOUSTIC MICROSCOPY

(71) Applicant: University of Florida Research Foundation, Incorporated, Gainesville, FL (US)

(72) Inventors: Huabei Jiang, Gainesville, FL (US); Chaolong Song, Gainesville, FL (US); Lei Xi, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 73 days.

(21) Appl. No.: 14/296,858

(22) Filed: Jun. 5, 2014

(65) Prior Publication Data

US 2015/0355444 A1 Dec. 10, 2015

(51) Int. Cl.
| | |
|---|---|
| G02B 21/00 | (2006.01) |
| G02B 21/02 | (2006.01) |
| G01N 29/06 | (2006.01) |
| G02B 3/14 | (2006.01) |
| G10K 11/30 | (2006.01) |

(Continued)

(52) U.S. Cl.
CPC ....... *G02B 21/0028* (2013.01); *G01N 29/0681* (2013.01); *G01N 29/221* (2013.01); *G01N 29/2418* (2013.01); *G02B 3/14* (2013.01); *G02B 21/0036* (2013.01); *G02B 21/02* (2013.01); *G10K 11/30* (2013.01)

(58) Field of Classification Search
CPC .......... G02B 21/0028; G02B 21/0026; G02B 21/02; G02B 21/0052; G02B 21/006; G02B 21/0072; G02B 21/33; G02B 3/12; G02B 3/14; G02B 21/0036; G01N 29/06; G01N 29/0654; G01N 29/0681; G01N 29/22; G01N 29/2418; G01N 29/2425; G01N 2291/028; G01N 2291/26; G01N 21/1702; G01N 29/221; G10K 11/26; G10K 11/30; G10K 11/32; G10K 15/046; G10K 2200/11; G02F 1/0131; G02F 1/11; G02F 1/125; G02F 1/33; G02F 1/335; G01S 15/8965
See application file for complete search history.

(56) References Cited

U.S. PATENT DOCUMENTS

| | | | | |
|---|---|---|---|---|
| 5,436,766 A | * | 7/1995 | Leary | ........ G02B 3/12 359/665 |
| 2012/0327286 A1 | * | 12/2012 | Imura | ........ G03B 17/00 348/335 |
| 2013/0041247 A1 | * | 2/2013 | Maswadi | ........ A61B 5/0095 600/407 |

(Continued)

OTHER PUBLICATIONS

Song, et al., "Acoustic lens with variable focal length for photoacoustic microscopy," Journal of Applied Physics, 2013, vol. 114, pp. 194703-1 through 194703-5.*

(Continued)

*Primary Examiner* — Stephone B Allen
*Assistant Examiner* — Adam W Booher
(74) *Attorney, Agent, or Firm* — Thomas Horstemeyer, LLP

(57) ABSTRACT

A lens system for use with photoacoustic microscopy apparatus has a collimated single mode optical fiber to which a toroidal ultrasound transducer is operatively attached. The transducer is located inside a tank. A lens housing is located inside the tank adjacent the transducer and has flexible optically transmissive entrance and exit ports made of polydimethysiloxane. The lens housing is filled with cinnamaldehyde. The cinnamaldehyde can be introduced into the lens housing and withdrawn from it so as to flex its entrance and exit ports, and the tank is filled with a mixture of glycerol and water.

15 Claims, 3 Drawing Sheets

FIG. 2

(51) Int. Cl.
*G01N 29/22* (2006.01)
*G01N 29/24* (2006.01)

(56) References Cited

U.S. PATENT DOCUMENTS

2014/0356897 A1* 12/2014 Wang .................. G01N 21/33
435/29

OTHER PUBLICATIONS

Song, et al., "Liquid acoustic lens for photoacoustic tomography," Optics Letters, vol. 38, No. 15, Aug. 1, 2013, pp. 2930-2933.*
"Physical Properties of Glycerine and Its Solutions," Glycerine Producers' Association, 1963, p. 1.*
"Lens-Maker's Formula," HyperPhysics, http://hyperphysics.phy-astr.gsu.edu/hbase/geoopt/lenmak.html, available online at least as of Feb. 21, 2001, accessed Dec. 18, 2015.*
Kinsler, et al., Fundamentals of Acoustics, Fourth Edition, 2000, pp. 121 and 135-136.*
"Speed of Sound in some common Liquids," The Engineering Toolbox, http://www.engineeringtoolbox.com/sound-speed-liquids-d_715.html, available online at least as of Feb. 10, 2012, accessed Dec. 18, 2015.*
"An ultra-thin PDMS membrane as a bio/micro-nano interface: fabrication and characterization," Biomed Microdevices, 2007, No. 9, pp. 587-595.*
Applied Optics, vol. 32, No. 22, pp. 4181-4186 (1993).
Journal of the Acoustical Society of America, vol. 49, No. 1 (Part 2), pp. 253-261 (1971).

* cited by examiner

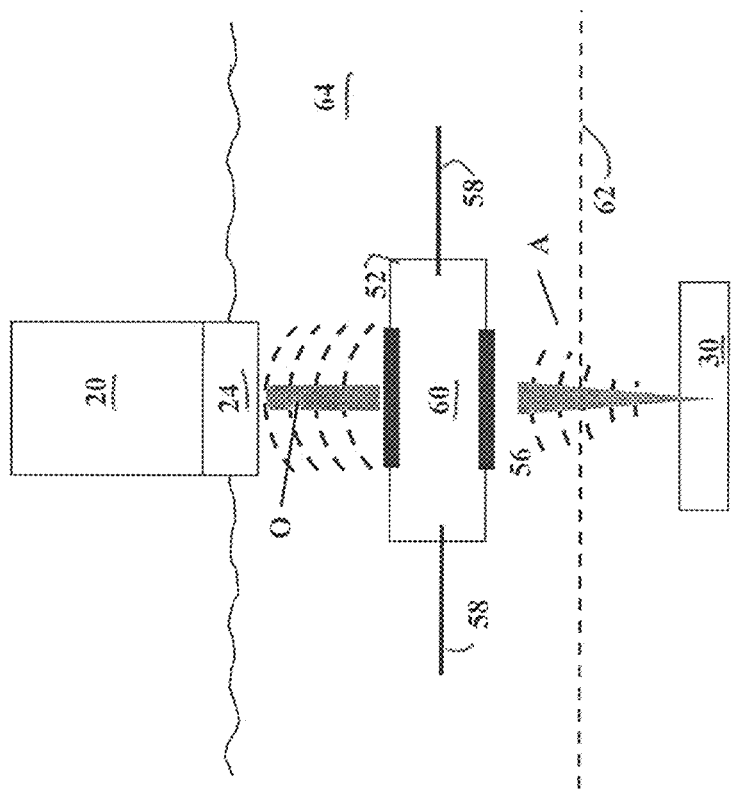

COMPACT LENS SYSTEM FOR USE IN PHOTOACOUSTIC MICROSCOPY

BACKGROUND OF THE INVENTION

The invention relates to microscopy, and more particularly relates to photoacoustic microscopy. In its most immediate sense, the invention relates to a lens system for use with compact confocal photoacoustic microscopy apparatus.

Photoacoustic microscopy ("PAM") is an imaging technique that uses back-reflected optical data and ultrasound data. In a confocal PAM system, the optical and ultrasound are both focused on the same point within the region of interest.

PAM apparatus is of two types: acoustic-resolution PAM ("ARPAM") and optical-resolution PAM ("ORPAM"). Both types require the use of linear scanning in order to acquire depth information in the image. In an ARPAM device, a focused ultrasound transducer is mechanically moved to scan the region of interest; in an ORPAM device, the scanning is carried out by moving a laser beam back and forth. These devices focus the ultrasound and laser light using different components, creating complicated and bulky lens systems.

It would be advantageous to provide a lens system for use with photoacoustic microscopy apparatus that was simpler and more compact than existing lens systems and that did not require mechanical scanning to acquire depth information within the volume of interest.

SUMMARY OF THE INVENTION

The invention proceeds from the realization that by using a lens made up of a liquid-filled deformable housing, the axial optical focus of the system can be adjusted by deforming the housing. This eliminates the need for mechanical scanning to acquire depth information; to do this, it is only necessary to deform the housing (as by introducing liquid therein or removing it therefrom).

Advantageously, the lens liquid is cinnemaldehyde, and the lens is located in a tank filled with a mixture of glycerol and water. By adjustment of the relative quantities of glycerol and water, equal optical and acoustic relative refractive indices can be produced. In this way, the acoustic focus and the optical focus can be made coincident (be made "confocal").

Furthermore, by using a lens liquid having a high index of refraction (cinnemaldehyde has a refractive index of 1.63), the focal length of the lens system can be shortened, thereby making the lens system more compact. Additionally, the use of such a lens liquid enlarges the numerical aperture of the system, which enhances its resolving capability.

BRIEF DESCRIPTION OF THE DRAWINGS

A preferred embodiment of the invention is schematically illustrated in the non-limiting drawings, in which:

FIG. 2 is a schematic illustration of a preferred embodiment of the invention.

DETAILED DESCRIPTION OF PREFERRED EMBODIMENTS

Figure 1:
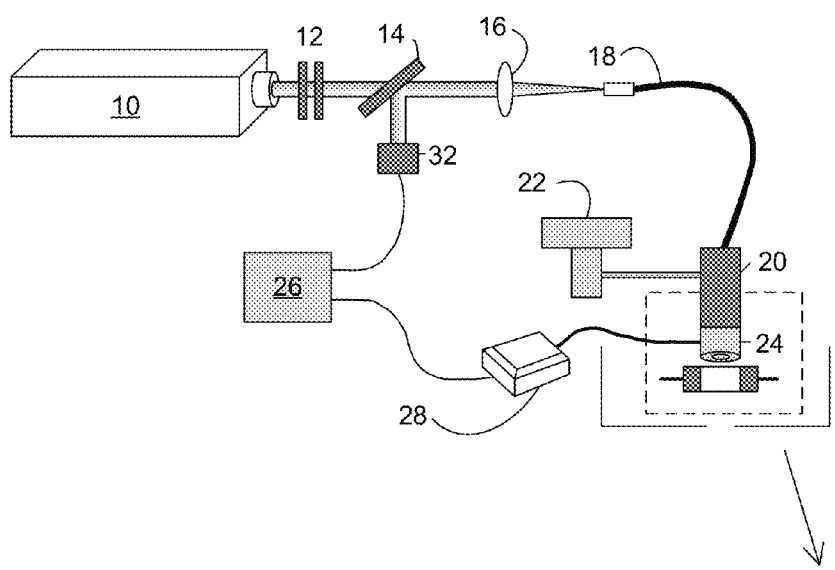
FIG. 1 shows an ORPAM imaging apparatus with which a preferred embodiment of the invention is installed.

An ORPAM imaging apparatus uses a laser 10 (in this example, an Nd:YAG pulsed laser, but this is only preferred and is not part of the invention) which directs pulses of light through neutral density filters 12 to a beam splitter 14. After passing through the beam splitter 14, the laser beam is focused by a lens 16 and directed into a fiber optic 18, which advantageously but not necessarily is a single mode fiber optic.

The fiber optic 18 has a collimator 20 located at its distal end, and the collimator 20 is moved back and forth within a two-dimensional plane by a two-dimensional actuator 22 that scans in the X-Y plane. At the distal end of the collimator 20 is located a toroidal ultrasound transducer 24.

Figure 3:
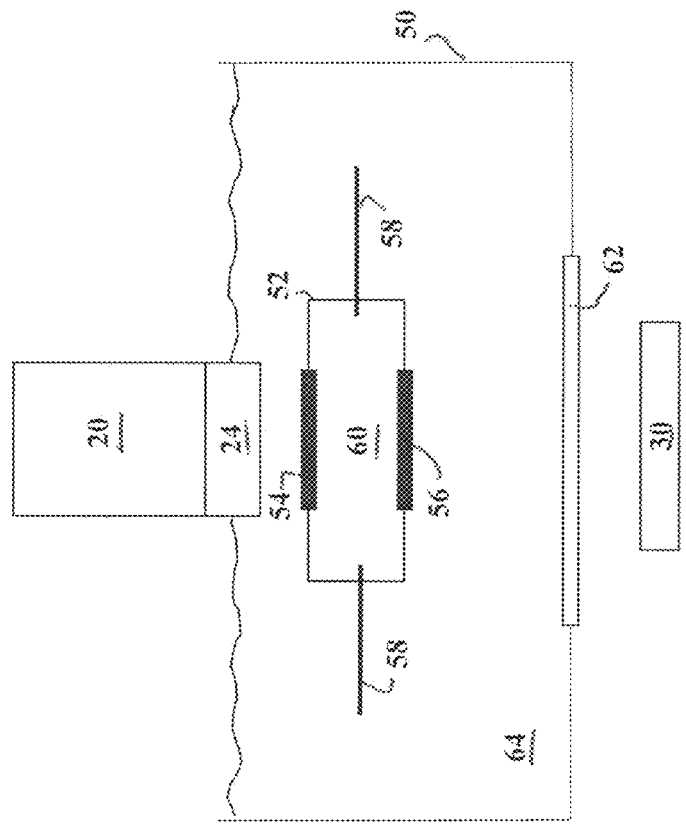
FIG. 3 schematically illustrates how the acoustic and optical beams propagate through a preferred embodiment of the invention.

Just as the laser 10 generates pulses of laser light, a computer 26 triggers generation of acoustic ultrasound pulses (shown schematically as A in FIG. 3). Signals from the computer 26 are amplified in an amplifier 28 and routed to the transducer 24, which produces pulses of ultrasound.

Laser light that is reflected back from a specimen 30 passes through the collimator 20, the fiber optic 18, and the lens 16 to become incident upon the beam splitter 14 (the optical pulses of laser light are shown schematically as O in FIG. 3). From there, the reflected-back laser light is incident upon an ultrafast photodetector 32, which generates electrical signals that are routed to the computer 26. This provides image information about the specimen 30 in a particular X-Y plane within the specimen. And, ultrasound pulses detected by the transducer 24 are then converted to electrical signals and routed to the computer 26. The delay between the time that a particular ultrasound pulse is generated by the transducer 24 and the time that its reflected-back counterpart is received at the transducer 24 represents the depth along the Z axis within the specimen 30 at which the corresponding image information is acquired. It is therefore possible to form a three-dimensional image of the sample by scanning the sample 30 along three axes; the X and Y axes that are normal to the axis of the preferred embodiment of the invention as described below, and the Z axis that is along the axis of the below-described preferred embodiment.

The apparatus described above is conventional and not part of the invention. The invention is a lens system designed for use with such apparatus, and a preferred embodiment thereof will now be described.

A tank 50 contains a lens housing 52. The lens housing 52 is a rectangular parallelepiped having a flexible and optically transmissive entrance port 54 and a like flexible and optically transmissive exit port 56. Advantageously but not necessarily, the entrance and exit ports 54, 56 are made of polydimethysiloxane. A needle 58 allows lens liquid 60 (advantageously but not necessarily cinnamaldehyde) to be introduced into and withdrawn from the lens housing 52. The lens housing 52 is otherwise sealed, so when lens liquid 60 is introduced into the lens housing 52, the ports 54 and 56 tend to flex outwardly and when lens liquid 60 is withdrawn from the lens housing 52 the ports 54 and 56 tend to flex inwardly. (As will be seen below, this is how the axial focus of the inventive lens system is adjusted.) The ports 54 and 56 need not be separate components; in the herein-described preferred embodiment, the lens housing 52 was made entirely of polydimethysiloxane using a 3-D printer.

An imaging window 62 is located at the bottom of the tank 50 and the specimen 30 is located beneath the imaging window 62. (The window 62 may optionally be sealed with a membrane, not shown.) The tank 50 is filled with a tank liquid 64, which advantageously is a mixture of water and glycerol with the water accounting for 42% of the mixture by weight. The transducer 24 extends into the tank liquid 64.

To achieve the compact size of which the preferred embodiment of the invention is capable, it is advantageous to use cinnamaldehyde as the lens liquid 60. This is because cinnamaldehyde has a high (1.63) index of refraction, causing the lens made up of the lens housing 52 and the lens liquid 60 to have a short focal length. The short focal length of the lens also increases the numerical aperture of the preferred embodiment, which improves its resolution. However, use of cinnamaldehyde for the lens liquid 60 is not required. If the lens is pressurized so that ports 54, 56 are convex (i.e. bulge outwardly), use of a liquid with a high index of refraction will converge the optical and ultrasound radiation. Alternatively use of a liquid with a reduced index of refraction will make the lens into a diverging lens.

To make the preferred embodiment of the invention confocal (see FIG. 3), the tank liquid 64 should have equal optical and acoustic relative refractive indices. In the preferred embodiment, this is achieved by making the tank liquid 64 a mixture of water and glycerol with the water being 42% by weight.

In experiments, the preferred embodiment of the invention achieved a numerical aperture of 0.43 and a focal length of 18 mm.

Although the invention has been illustrated as being used with an ORPAM system, it can also be used with an ARPAM system. In that case, the fiber optic 18 would likely be implemented using an optical fiber bundle.

A preferred embodiment of the invention has been described above, but the invention is defined only by the following claims:

The invention claimed is:

1. A lens system for use with photoacoustic microscopy apparatus, comprising:
   a fiber optic with a collimated distal end;
   a tank comprising an imaging window;
   a toroidal ultrasound transducer located inside the tank and operatively secured to the collimated distal end of the fiber optic;
   a lens housing located inside the tank and adjacent the toroidal ultrasound transducer, the lens housing having flexible optically transmissive entrance and exit ports aligned between the toroidal ultrasound transducer and the imaging window;
   a lens liquid filling the lens housing;
   a fluid connection located inside the tank for deforming the lens housing, the fluid connection configured to introduce or withdraw the lens liquid to or from the lens housing to flex the entrance and exit ports of the lens housing; and
   a tank liquid completely filling the tank and surrounding the lens housing.

2. The lens system of claim 1, wherein the lens liquid has an index of refraction of at least 1.63.

3. The lens system of claim 2, wherein the lens liquid is cinnamaldehyde.

4. The lens system of claim 1, wherein the tank liquid has acoustic and optical refractive indices that produce coincident acoustic and optical foci.

5. The lens system of claim 1, wherein the fiber optic is a single mode optical fiber.

6. The lens system of claim 1, wherein the entrance and exit ports of the lens housing are of polydimethysiloxane.

7. The lens system of claim 1, wherein the tank liquid is a mixture of glycerol and water.

8. The lens system of claim 7, wherein a weight percentage of the water is 42% of the mixture.

9. The lens system of claim 1, wherein the fluid connection for deforming the lens housing comprises a needle for introducing and removing the lens liquid to or from the lens housing.

10. The lens system of claim 1, wherein the fiber optic is an optical fiber bundle.

11. The lens system of claim 1, wherein the imaging window is sealed with a membrane.

12. The lens system of claim 1, wherein the toroidal ultrasound transducer is secured to a collimator located at the collimated distal end of the fiber optic.

13. The lens system of claim 12, wherein the collimator is positioned by a two-dimensional actuator.

14. The lens system of claim 1, wherein a specimen is positioned adjacent to the imaging window of the tank.

15. The lens system of claim 14, wherein laser light provided via the fiber optic is reflected back from the specimen through the entrance and exit ports of the lens housing.

* * * * *